(12) United States Patent
Small et al.

(10) Patent No.: US 10,307,341 B2
(45) Date of Patent: Jun. 4, 2019

(54) MEDICAL TUBE POSITION CONFIRMATION DEVICE

(71) Applicant: NGPod Global Limited, Blackpool (GB)

(72) Inventors: David Raymond Small, Blackpool (GB); John Davies, Blackpool (GB)

(73) Assignee: NGPod Global Limited, Daresbury, Cheshire (GB)

( * ) Notice: Subject to any disclaimer, the term of this patent is extended or adjusted under 35 U.S.C. 154(b) by 18 days.

(21) Appl. No.: 15/440,933

(22) Filed: Feb. 23, 2017

(65) Prior Publication Data

US 2017/0239149 A1 Aug. 24, 2017

(30) Foreign Application Priority Data

Feb. 23, 2016 (GB) .................................. 1603131.2

(51) Int. Cl.
*A61B 5/00* (2006.01)
*G02B 6/02* (2006.01)
(Continued)

(52) U.S. Cl.
CPC ......... *A61J 15/0088* (2015.05); *A61B 5/0084* (2013.01); *A61B 5/1459* (2013.01);
(Continued)

(58) Field of Classification Search
CPC .............. A61B 5/0084; A61B 5/14507; A61B 5/14539; A61B 5/1459; A61B 5/6871;
(Continued)

(56) References Cited

U.S. PATENT DOCUMENTS

| 4,954,318 | A | * | 9/1990 | Yafuso | ............... | G01N 21/7703 |
| | | | | | | 250/227.11 |
| 5,114,676 | A | | 5/1992 | Leiner et al. | | |
| 5,127,077 | A | | 6/1992 | Iyer et al. | | |
| 5,152,287 | A | * | 10/1992 | Kane | ................... | A61B 5/1459 |
| | | | | | | 204/415 |

(Continued)

FOREIGN PATENT DOCUMENTS

| EP | 2412311 | 1/2012 |
| WO | 2015092733 | 6/2015 |

OTHER PUBLICATIONS

GB1603131.2 Search Report from the United Kingdom Intellectual Property Office dated Jul. 26, 2016 (5 pages).
(Continued)

*Primary Examiner* — Michael P Mooney
(74) *Attorney, Agent, or Firm* — Michael Best & Friedrich LLP (57) ABSTRACT

A feeding tube position confirmation device 102, operable to confirm the position of a predetermined portion of a medical feeding tube in a predetermined portion of a human or animal body, the position confirmation device comprising an optical waveguide 106 dimensioned to be insertable into the lumen of the feeding tube, the optical waveguide having a sensing distal end 108 comprising a distal end material and a sensing material mixed with the distal end material, the sensing material operable to provide a change in optical properties at the distal end 110 of the optical waveguide dependent on the environment to which the sensing distal end 108 of the waveguide is exposed. The sensing material may comprise a reflective material. Methods of manufacture and use of such devices are also described.

9 Claims, 3 Drawing Sheets

(51) Int. Cl.
*G02B 6/44* (2006.01)
*A61B 5/145* (2006.01)
*A61J 15/00* (2006.01)
*G01N 21/77* (2006.01)
*G01N 21/78* (2006.01)
*G01N 21/80* (2006.01)
*A61B 5/1459* (2006.01)

(52) U.S. Cl.
CPC ...... *A61B 5/14507* (2013.01); *A61B 5/14539* (2013.01); *A61B 5/6871* (2013.01); *A61J 15/0003* (2013.01); *G01N 21/7703* (2013.01); *G01N 21/78* (2013.01); *G02B 6/02033* (2013.01); *G02B 6/4415* (2013.01); *A61B 2562/12* (2013.01); *A61J 15/0069* (2013.01); *G01N 21/80* (2013.01)

(58) Field of Classification Search
CPC .............. A61B 2562/12; A61J 15/0003; A61J 15/0069; A61J 15/0088; G01N 21/7703; G01N 21/78; G01N 21/80; G02B 6/4415; G02B 6/02033
USPC ............................................. 385/12–13, 117
See application file for complete search history.

(56) References Cited

U.S. PATENT DOCUMENTS

| | | | |
|---|---|---|---|
| 5,262,192 A | | 11/1993 | Nelson et al. |
| 5,277,872 A | * | 1/1994 | Bankert ............. A61B 5/14539 385/12 |
| 5,326,531 A | * | 7/1994 | Hahn .................... A61B 5/1455 385/123 |
| 5,900,215 A | | 5/1999 | Seifert et al. |
| 6,159,536 A | | 12/2000 | Kimball et al. |
| 2009/0275825 A1 | * | 11/2009 | Thomas ............. A61B 5/14539 600/424 |
| 2010/0030133 A1 | | 2/2010 | Elia et al. |

OTHER PUBLICATIONS

GB1603131.2 Search Report from the United Kingdom Intellectual Property Office dated Sep. 8, 2016 (3 pages).
GB1702923.2 European Combined Search and Examination Report from the United Kingdom Intellectual Property Office dated Mar. 24, 2017 (7 pages).
PCT/GB2017/050464 International Search Report and Written Opinion of the International Searching Authority dated Apr. 26, 2017 (14 pages).

* cited by examiner

MEDICAL TUBE POSITION CONFIRMATION DEVICE

BACKGROUND

This application claims priority to United Kingdom Patent Application No. 1603131.2, filed Feb. 23, 2016, the entire contents of which are hereby incorporated by reference herein.

BACKGROUND

The present invention relates to medical tubes, such as, for example, nasogastric and nasointestinal feeding tubes, and particularly the confirmation of correct placement and/or avoidance of misplacement of the portion of the tube through which the fluid exits.

In healthcare, human or animal patients may be incapable of feeding themselves by conventional means. In such circumstances it is necessary to deliver nutrients into the stomach or small intestine by way of a feeding tube. This is generally carried out by passing a tube through the patient's nasal passage and into the stomach or the small intestine by way of the gastrointestinal tract. The distal end of such feeding tubes comprise one or more fluid output apertures, which act to deliver fluid nutrients to predetermined locations such as, for example, the stomach or small intestine. Correct positioning of the fluid output apertures within the stomach or small intestine is essential for the safety of the patient. For example, misdirection of the feeding tube upon insertion via the nasal cavity such that the leading end of the feeding tube is directed towards the lungs may occur, particularly with patients who have an inhibited cough or gag reflex such as, for example, the critically ill and premature babies. Such misplacement of the fluid output apertures may, upon feeding, lead to serious pleuropulmonary complications such as, for example, pneumonia, abscess and empyema.

Also, in certain circumstances it may be necessary for certain fluid nutrients are delivered to specific parts of the digestive system such as, for example, specifically to the stomach and/or specifically to the small intestine. Again, correct placement of the fluid outlet apertures is essential.

Generally, health practitioners currently approximate for the position of the fluid output apertures before confirming the correct position.

A commonly used method for approximating correct placement of the fluid output apertures is to connect a syringe to the proximate end of a pre-placed feeding tube and aspirate a quantity of fluid from the region around the fluid output apertures. The pH of the aspirated fluid is then measured using pH paper to determine whether, for example, the pH of the fluid corresponds with the pH of gastric fluid from the stomach thereby confirming placement of the fluid output apertures in the stomach. This method is currently recommended by the National Patient Safety Agency (NPSA) in the United Kingdom for use in the UK National Health Service (NHS), in addition to confirmation using X-Ray if the pH test is inconclusive.

Despite the publication of the NPSA recommendations, there has remained an unsatisfactory number of deaths and harm due to misplaced NG feeding tubes occurring in the NHS. Moreover, the cases of misplaced NG feeding tubes has not only been as a result of the bedside procedure but also from the misinterpretation of X-Rays [National Patient Safety Agency (NPSA): Patient Safety Alert; NPSA/2011/PSA002].

The NHS considers misplaced NG feeding tubes to be such a problem that it has been listed on the NHS "Never Events" list since it was first introduced in 2009 [NPSA; Never Events Framework 2009/10, page 5].

The NHS is consistently monitored and managed for best practice. However, such monitoring and management does happen in most countries throughout the world. Consequently, it is envisaged that the number of deaths and harm caused by misplaced feeding tubes is at least proportional to that of the NHS and probably greater.

The currently NPSA recommended pH test is disadvantaged for a number of reasons. It is often difficult to obtain sufficient fluid by aspiration to carry out the test, which can distress the patient and result in delayed feeding which is detrimental to the wellbeing of the patient. The quality of the test is relative to the competence, diligence and interpretation of the individual health professional undertaking the test. It is known for the aspirated gastric fluid to become contaminated as it is transferred from the syringe to the pH paper, leading to false readings. Furthermore, significant care has to be taken not to aspirate too much fluid. Also this method can be unpleasant for the patient as it can tend to induce reflux and vomiting which can lead to further complications. Where the pH test is inconclusive, the patient cannot be fed and X-Ray must be used to confirm correct placement. However, X-Ray is relatively expensive, as it requires a radiographer, X-Ray equipment and also a doctor to confirm correct placement. Moreover, recent studies have shown that a high number of misplaced feeding tubes have been missed due to misinterpretation of X-Rays. Furthermore, this method is further disadvantaged in that the patient, who may be critically ill, may also have to be transferred to a radiology department and is also exposed to X-Ray.

Another method, which the NPSA has specifically recommended should not be used, is the so-called woosh method, which involves using a syringe to inject air into the proximate end of a pre-inserted feeding tube. The health practitioner then listens using a stethoscope around the stomach region for a wooshing noise to confirm the fluid exit apertures of the tube are located in the stomach. However, although widely used outside the United Kingdom, studies have shown that the woosh test does not provide sufficient accuracy of confirmation that the fluid exit apertures of the tube are actually in the stomach when the woosh noise can be heard by the health practitioner. Patent document number U.S. Pat. No. 5,085,216 describes a feeding tube assembly for nasogastric and nasointestinal feeding comprising a pH indicator carried by a stiffener used for inserting the feeding tube into a patient. After insertion of the leading end of the feeding tube into an approximated desired position the pH indicator is withdrawn and examined for a pH corresponding to that of the stomach thereby indicating that the end of the tube is positioned in the stomach. However, this feeding tube assembly is disadvantaged in that it is necessary to approximate the correct position of the tube prior to withdrawing the pH indicator to determine whether or not the tube is correctly positioned. If the tube is not correctly positioned in the stomach it is necessary to withdraw the tube from the patient and repeat the whole procedure again using a complete new feeding tube assembly which is undesirably wasteful, time consuming and distressful for the patient Furthermore, the pH indicator may become contaminated as it is withdrawn into the environment external to the body leading to false and unreliable pH readings.

Patent document number U.S. Pat. No. 4,381,011 discloses a system and method for feeding of fluid into a preselected portion of the gastro intestinal tract of a patient. The system comprises a tube with a pH measuring device positioned thereon, a monitoring device, capable of processing pH signals to determine the position of the tube, and a fluid feed control. Initial positioning of the tube and subsequent monitoring of the position of the tube is accomplished by receiving and processing pH signals from the pH measuring device positioned proximate the distal end of the tube and connected to the monitoring device. The tube may be selectively positioned in a preselected portion of the digestive system by monitoring the pH, which the pH measuring device is measuring, and comparing those measurements with known values of pH for specific portions of the digestive system. However, this system is disadvantaged in that it is relatively expensive, needing pH measuring devices and monitors, and requires an external electrical power supply.

Patent document number EP2412311A2 describes a feeding tube position confirmation device having an input optical waveguide and an output optical waveguide dimensioned to be insertable into the lumen of a feeding tube. A sensor is disposed on the optical waveguides at a position which corresponds to the predetermined portion of the feeding tube. The sensor means has a colour change indicator operable to change colour relative to the chemical content of the environment proximate thereto. In use, the input optical waveguide carries light to the sensor means. The sensor means causes a change in the colour of the input light to provide an output light of a predetermined colour indicative of the position of the feeding tube. The output light is carried to the proximate end of the position confirmation device, by the output optical waveguide, at which it is viewed by the user to determine the position of the tube in the human or animal body.

Although this device is relatively simple, it is relatively difficult to manufacture in a repeatable manner in that it is difficult to form a robust and repeatable colour sensor disposed on the end of the input and output optical waveguides. Moreover, unless a robust and strong attachment is able to be established between the optical waveguide and the sensor there is a danger that in use, the sensor may become detached from the waveguide. Also, both an input and output optical waveguide is required in order to return sufficient light from the sensor to the proximate end of the position confirmation device. This is particularly disadvantageous because the diameter of the device needs to be as small as possible in order to be applicable to all sizes of NG feeding tube, including small French size tubes.

It is therefore desirable in the industry for there to be a feeding tube position confirmation device which is easy to use, robust, reliable, applicable to all sizes of tubes, relatively inexpensive to manufacture and capable of indicating correct positioning of a tube during insertion of the tube, and which does not require an electrical mains power source.

SUMMARY

In an aspect of the invention is provided a feeding tube position confirmation device, operable to confirm the position of a predetermined portion of a medical feeding tube in a predetermined portion of a human or animal body, the position confirmation device comprising an optical waveguide dimensioned to be insertable into the lumen of the feeding tube, the optical waveguide having a sensing distal end comprising a distal end material, and a sensing material mixed with the distal end material, the sensing material operable to provide a change in optical properties at the distal end of the optical waveguide dependent on the environment to which the sensing distal end of the waveguide is exposed.

Suitably, the optical waveguide is capable of being inserted into the lumen of the feeding tube. It will be appreciated that the optical waveguide has a proximal end which is capable of allowing light to enter the waveguide from a light source and/or allowing light from the sensing distal end to exit the waveguide for detection.

Because the sensing material is intermixed with the distal end material of the waveguide, a robust and strong attachment between the optical waveguide and the sensing material is provided, reducing or avoiding risk of detachment of the sensing material from the waveguide in use.

The sensing material suitably comprises an optical indicator, optionally a chemical and/or biological indicator, such as a pH indicator. In embodiments, the sensing material is operable to change to a predetermined colour dependent on the environment to which the sensing distal end of the waveguide is exposed. For instance, the sensing material may be operable to change to a predetermined colour upon exposure of the sensing distal end to an environment having a pH of 5.5 or less, 5 or less, 4.5 or less, 4 or less, 3.5 or less, or 3 or less. Typically the sensing material is operable to change to a predetermined colour upon exposure of the sensing distal end to an environment having a pH of 4 or less.

Suitable chemical or biological indicators include one or more of: Thymol Blue, Methyl Red, Bromothymol Blue, Phenolphthalein, Bromocresol green, Fluorescein, Ether, or Universal Indicator. Other suitable indicators will become apparent to the skilled person on reading the present disclosure depending on the particular environment (i.e. physical or chemical environment) which is deemed to be indicative of the desired final location of the feeding tube. The chemical or biological indicator may change colour or other optical characteristic depending on the presence of specific predetermined markers such as, for example, pH level or Biological Markers such as Human Gastric Lipase, Pepsin, Intrinsic Factor, Mucin and Gastrin.

In typical embodiments, the sensing material comprises an optical indicator mixed with a polymer (e.g. dispersed or dissolved within a polymer). The optical indicator may be any suitable indicator capable of demonstrating a detectable change in optical properties in response to an environmental stimulus, such as a change in pH. Exemplary optical indicators are capable of changing colour in response to the stimulus, e.g. in response to a change in pH. The optical indicator may be one or more of those defined herein, e.g. a chemical/biological indicator such as a pH indicator.

In preferred embodiments, the sensing material further comprises a reflective material. The reflective material may be any suitably reflective material. The skilled person will appreciate that for insertion into the human or animal body the reflective material should be suitably non-toxic, e.g. the reflective material may be selected from one or more biologically inert materials, such as biologically inert metal oxides. A preferred reflective material is titanium dioxide. Thus, in preferred embodiments, the reflective material comprises, consists essentially of, or consists of titanium dioxide. The reflective material may be provided in the form of reflective particles. The particles may for instance have a maximum diameter of 100 µm or less, optionally 90 µm, 80 µm or less, 70 µm or less, 60 µm or less, 50 µm or less, 40 µm or less, 30 µm or less, 20 µm or less, or 10 µm or less. In embodiments, the mean particle diameter is 50 µm or less, 40 µm or less, 30 µm or less, 20 µm or less, or 10 µm or less, e.g. 10 µm or less. In embodiments, the reflective material may be mixed with a polymer. In embodiments wherein the sensing material comprises an optical indicator mixed with a polymer, the reflective material is preferably also mixed with the polymer. For instance, the optical indicator and reflective material may be dispersed within the same polymer matrix. The inventors have discovered that particularly advantageous effects can be obtained when a reflective material is used, especially where the reflective material is mixed with an optical indicator in the sensing material. In particular, the use of a reflective material mixed with the optical indicator at the sensing distal end of the waveguide improves the strength of the optical signal returning up the waveguide to be detected/observed by a user.

The sensing material may suitably comprise one or more brightening agents (to enhance reflectivity). A preferred brightening agent for use in the present invention is barium sulphate. The sensing material may thus preferably comprise barium sulfate. In embodiments, the reflective material may be mixed with a polymer. In embodiments wherein the sensing material comprises an optical indicator mixed with a polymer and/or a reflective material mixed with the polymer, the brightening agent is preferably also mixed with the polymer, e.g. they may be dispersed within the same polymer matrix. The brightening agent may be provided as distinct particles, or may be used to coat the reflective material (e.g. in the case of transparent brightening agents). The use of a brightening agent together with the reflective material also further improves the optical efficiency of the device.

In a preferred embodiment, the sensing material comprises a polymer, brightening agent, chemical indicator and reflective material. The sensing material may thus comprise thermo-stable polyurethane, barium sulphate, Bromocresol green and titanium dioxide. The relative ratios of the various components of the sensing material can be determined by the skilled person. The sensing material may, for instance, contain about 96% polymer, about 0.4% brightening agent, about 0.4% chemical indicator and about 2.5% reflective material. The sensing material may, for instance, contain about 96% hydrophilic polyurethane, about 0.4% barium sulphate, about 0.4% Bromocresol green and about 2.5% titanium dioxide.

The polymer may be any suitable biocompatible polymer. Preferably, the polymer is a hydrophilic polyurethane, e.g. a thermostable polyurethane. Where a polymer is used, the polymer is preferably chosen/formulated so as to be able to allow water and small molecules (e.g. acids/bases) to pass into the polymer matrix (so as to contact any optical indicator bound within the polymer matrix).

In embodiments, the thickness of the sensing material on the distal end of the optical waveguide is from 50 µm-300 µm to achieve desirable levels of optical output. The thickness may be from 75 µm-275 µm, or preferably from 100 µm to 300 µm. However, the skilled person will appreciate that the thickness of material will depend on the nature of the sensing material, e.g. the concentration of optical indictor in the sensing material and the form of change in optical characteristic to be detected.

Suitably, the distal end material of the optical waveguide comprises a distal end polymer. The distal end polymer is typically the same polymer from which the main body of the waveguide is formed, but may alternatively be a polymer provided at the distal end that is different to the material used to form the main body of the waveguide. Suitable polymers for use in waveguides according to the present invention will be apparent to the skilled person. The distal end polymer may be any suitable inorganic or organic polymer that allows the transmission of light, such as inorganic or organic glass. Preferably, the distal end polymer is an organic polymer, e.g. an organic glass. In a particularly preferred embodiment, the distal end material comprises, consists essentially of, or consists of a polyalkylcarboxylate, such as polymethylmethacrylate ("PMMA").

In embodiments wherein the sensing material comprises a polymer, and the distal end material comprises a polymer, the mixing of the sensing material and distal end material as described herein thus provides intermixing of the respective polymer matrices. This provides a robust bond between the sensing material and distal end material of the waveguide to form a robust sensing distal end. In embodiments wherein the sensing material comprises a polymer and the distal end material comprises a polymer, the sensing material polymer may be the same as the distal end material polymer, or it may be different. Typically, the sensing material polymer is different to the distal end material polymer. In an example, the sensing material polymer comprises, consists essentially of, or consists of a hydrophilic polyurethane (preferably a thermostable polyurethane) and the distal end material polymer comprises, consists essentially of, or consists of a polyalkylcarboxylate (preferably polymethylmethacrylate ("PMMA")).

The sensing distal end of the optical waveguide may be formed by coating the distal end of an optical waveguide with the sensing material, transforming the coated distal end into a fluid state such that the sensing material and distal end material are mixed with each other and then transformed into a solid state to form the sensing distal end. For instance, according to an embodiment of the present invention there is provided a feeding tube position confirmation device, operable to confirm the position of a predetermined portion of a medical feeding tube in a predetermined portion of a human or animal body, the position confirmation device comprising an optical waveguide dimensioned to be insertable into the lumen of said feeding tube, the optical waveguide having a sensing distal end comprising a sensing material operable to change to a predetermined colour relative to the chemical content of the environment to which it is exposed and thereby cause a change in the colour of light incident thereon dependent on the environment to which the sensing distal end of the waveguide is exposed, wherein the sensing distal end of the optical waveguide is formed by coating the distal end of the optical waveguide with the sensing material, transforming the coated distal end into a fluid state such that the sensing material and distal end material are mixed with each other and then transformed into a solid state to form a sensing distal end.

The distal end may be transformed into a fluid state by dipping into a solvent solution. The solvent may be any solvent as described herein. The solvent solution may comprise a solvent (which may be as defined herein) and sensing material. The solvent solution may advantageously comprise Dichloromethane; Tetrahydrofuran or Dioxane and sensing material. In some embodiments the solution comprises methanol and sensing material.

Alternatively, the sensing distal end may be transformed by heating it to a temperature in the range of 175 to 250° C. More preferably, the sensing distal end may be transformed by heating it to a temperature of approximately 232° C.

In embodiments, the sensing distal end of the optical waveguide is formed by a process comprising:
 a. contacting the distal end of an optical fibre with a fluid coating composition, the fluid coating composition comprising the sensing material dispersed or dissolved in a solvent (optionally wherein the composition is in the form of a sol-gel), wherein the solvent is capable of at least partially fluidising or swelling the distal end material of the optical fibre such that at least some mixing of the distal end material and sensing material occurs; and b. removing solvent from the fluid coating composition in contact with the distal end and solidifying the sensing distal end to provide an optical fibre having a sensing distal end comprising a distal end material, and a sensing material mixed with the distal end material.

The removing of solvent and solidification may be performed separately or simultaneously. For instance, heating or vacuum induced evaporation may cause the removal of solvent and consequent solidification.

Suitably, the solvent in the embodiments described herein (e.g. for use in dipping, dispersing or dissolving as described) may be an organic solvent. Suitably the solvent is capable of at least partially fluidising or swelling the distal end material of the optical fibre. In embodiments, the solvent is selected from alcohols, ethers, esters, halo-substituted hydrocarbons, and mixtures thereof. The solvent may be selected from $C_{1-6}$ alcohols, $C_{1-6}$ ethers, halo-substituted $C_{1-6}$ hydrocarbons, and mixtures thereof. The term "alcohol" includes branched or unbranched, cyclic or acylic compounds containing one or more hydroxyl groups. The alcohol may contain multiple hydroxyl groups but typically contains only one. The alcohol may contain one or more heteroatoms or heteroatom-containing groups other than hydroxyl groups but typically does not. Suitable substituents include halides. Typically the alcohol is absent of heteroatoms other than in the hydroxyl group(s). Preferably the $C_{1-6}$ alcohol is a $C_{1-2}$ alcohol, such as methanol or ethanol, preferably methanol. The term "ether" includes branched or unbranched, cyclic or acylic ethers. The ether may contain multiple ether moieties but typically contains only one. The ether may contain one or more heteroatoms other than oxygen, e.g. one or more heteroatom-containing groups, but typically does not. Suitable substituents include halides. Preferably the ether is absent of heteroatoms other than oxygen. Preferably the $C_{1-6}$ alcohol is a cyclic ether, such as a cyclic $C_{5-6}$ ether, e.g. THF or dioxane. In embodiments, the solvent is selected from one or more of chloroform, dichloromethane, hexafluoroisopropanol, THF, dioxane, ethanol and methanol, preferably wherein the solvent is DCM, ethanol or methanol, more preferably methanol.

Depending on the solvent and/or sensing material and/or distal end material, some heating of the solvent above room temperature may be required in order to facilitate dispersal/solvation of the sensing material in the solvent, and/or to facilitate the fluidization/swelling of the distal end material. Heating may be typically required with more polar solvents, such as alcohols. For instance, methanol may be heated up to boiling (i.e. under reflux conditions). When the sensing material comprises a hydrophilic polyurethane and the distal end material comprises a polyalkylcarboxylate (e.g. PMMA), then methanol is a preferred solvent and the methanol is typically heated up to boiling (i.e. approx. 81° C.).

The sensing material according to any embodiment herein may be operable to change to a predetermined colour upon exposure of the sensing distal end to an environment having a pH of 6 or less, such as pH 5.5 or less. Alternatively, or additionally, the sensing material may be operable to change to a predetermined colour upon exposure of the sensing distal end to an environment having a pH of 4 or less.

The sensing material may be according to any description of the sensing material described herein. The sensing material may advantageously comprise Thermo-stable Polyurethane, Barium Sulphate, Bromocresol green and Titanium Dioxide. The sensing material may advantageously contain 96% Thermo-stable Polyurethane, 0.4% Barium Sulphate, 0.4% Bromocresol green and 2.5% Titanium Dioxide.

In the aspects and embodiments of the feeding tube position confirmation device of the invention, the optical waveguide has a proximal and distal end, wherein the distal end is a sensing distal end. The optical waveguide may further comprise an optical sensor at the proximal end of the optical waveguide operable to detect the change in optical properties at the distal end of the optical waveguide.

In some embodiments, the optical waveguide may comprise a single optical fibre operable as both an input and an output. Alternatively, the optical waveguide may comprise a plurality of optical fibres, wherein at least one optical fibre is operable as an input optical fibre and at least one optical fibre is operable as an output optical fibre.

The optical waveguide advantageously comprises a proximate end having an output connector operable to separate the optical waveguide into an input proximate waveguide end and an output proximate waveguide end and optically engage with a control unit.

Typically the feeding tube position confirmation device advantageously has sufficient rigidity such that it is operable as a stiffener to facilitate insertion of the feeding tube into the human or animal body.

According to a further aspect of the present invention there is provided a control unit operable to control a feeding tube confirmation device according to any of the aspects and embodiments disclosed herein. The control unit typically comprises an optical sensor operable to detect the change in optical properties at the distal end of the optical waveguide and provide an output capable of signaling a change in optical characteristics at the sensor to a user. In embodiments, the control unit comprises a processor and an optical sensor, wherein the optical sensor is operable to detect the change in optical properties at the distal end of the optical waveguide, and the processor is operable to receive characteristics of the change in optical properties from the optical sensor, determine from the characteristics whether or not the sensing distal end is positioned in the predetermined position of the human or animal body and indicate to a user if the sensing distal end is positioned in the predetermined position of the human or animal body.

In embodiments, the optical sensor is a light detector. For instance, in an embodiment of the control unit, the control unit comprises a processor, a light source and a light detector, wherein the light source is operable to illuminate the sensing distal end of the waveguide, the light detector is operable to receive output light from the optical waveguide, and the processor is operable to receive characteristics of the output light from the light detector, determine from the output light characteristics whether or not the sensing distal end is positioned in said predetermined position of the human or animal body and indicate to a user if the sensing distal end is positioned in the predetermined position of the human or animal body.

The control unit is advantageously operable to enable the light source to illuminate the sensing distal end with a pulse of light. The pulse of light is preferably in the range of 6 to 10 milliseconds. The pulse of light is more preferably of 8 milliseconds duration.

The light source advantageously illuminates the sensing distal end with white light with a wavelength in the range of 405 nm to 685 nm.

The light detector may be a Red-Green-Blue, RGB, detector.

The light detector may be operable to determine the intensity of the red, green and blue colours of the output light.

The processor advantageously uses the output light characteristics from the light detector to determine values for the hue, saturation and lightness of the output light received by the light detector and compare those values with predetermined values indicative of the distal sensing end being disposed in said predetermined position.

The processor is advantageously operable to confirm placement of the distal sensing end in the predetermined position upon determination that the hue is within a yellow parameter.

According to a further aspect of the present invention there is provided a medical feeding tube position confirmation kit comprising a medical feeding tube and at least one feeding tube position confirmation device as defined according to any aspect or embodiment disclosed herein.

In embodiments, the feeding tube position confirmation kit further comprises a control unit operable to control the device. The medical feeding tube position confirmation kit may for instance comprise a control unit according to any aspect or embodiment of the control unit described above.

According to a further aspect of the present invention there is provided a medical feeding tube position confirmation system comprising a device according to any aspect or embodiment of the feeding tube positioning device of the present invention described herein and a control unit according any aspect or embodiment of the control unit described above.

According to a further aspect of the present invention there is provided a method of manufacturing a feeding tube confirmation device comprising: providing a length of optical waveguide having a proximal end and a distal end; providing a quantity of sensing material and treating the distal end of the optical waveguide to mix the sensing material with the distal end material of the optical waveguide.

In an embodiment, treating the distal end of the optical waveguide to mix the sensing material with the material of the optical waveguide comprises: selecting a length of the distal end material; applying the sensing material to the selected length of the distal end; transforming the selected length of the distal end into a fluid state such as to cause the sensing material to mix with the material of the optical waveguide distal end; and transforming the distal end into a solid state to form a sensing distal end. In other words, the present invention also provides a method of manufacturing a feeding tube confirmation device comprising: providing a length of optical waveguide having a proximate end and a distal end; providing a quantity of sensing material; selecting a length from the distal end of the optical waveguide; applying a sensing material to the selected length of the distal end; transforming the selected length of the distal end into a fluid state such as to cause the sensing material to mix with the material of the optical waveguide distal end; and transforming the distal end into a solid state to form a sensing distal end.

Transforming the selected length of the distal end into a fluid state may comprise immersing the distal end into a solvent.

The solvent may comprise a solution comprising any of the respective solvents described herein and a sensing material. The solution may be of Dichloromethane, Tetrahydrofuran, methanol, or Dioxane and sensing material. The solution may be of Dichloromethane, Tetrahydrofuran or Dioxane and sensing material.

The duration of time for which the distal end should be immersed in solvent should be sufficient to cause the desired transformation, e.g. fluidization, of the distal end material but preferably not so long so as to have undesirable effects on the optical or chemical properties of the distal end material. For instance, prolonged exposure of certain polymers to certain solvents can cause brittleness, cracking and/or opacification and so the duration of exposure should be modified according to the material and solvent. Any undesirable reaction of the distal end material of the waveguide may be mitigated by minimizing the area of exposure of the distal end. For instance, the exposure may be constrained only to the very end tip of the waveguide. However, application to a greater length of the end of the waveguide is desirable to increase the optical signal. The distal end may for instance be immersed in the solvent for between 0.5 and 1.5 seconds. The distal end is preferably immersed in the solvent for approximately 1.0 seconds.

Following immersion of the distal end in the solvent, the distal end is removed from the solvent and may be dried. The drying may, for instance, be for a duration of between 1.5 Seconds and 2.5 Seconds. The distal end is, in embodiments, dried for a duration of approximately 2.0 Seconds.

Alternatively, the distal end may be transformed by heating to a suitable temperature so as to facilitate the transformation, depending on the particular distal end material used. The skilled person will be able to determine suitable temperatures for a given distal end material, e.g. for a given polymer. The distal end may for instance be transformed by heating it to a temperature in the range of 175 to 250° C. The sensing distal end is preferably transformed by heating it to a temperature of from 180 to 250° C., such as 200 to 240° C., more preferably 220 to 240° C., for instance approximately 232° C. The sensing material may be any suitable sensing material as defined herein. The sensing material may for instance comprise Thermo-stable Polyurethane, Barium Sulphate, Bromocresol green and Titanium Dioxide. The sensing material may advantageously contain 96% Thermo-stable Polyurethane, 0.4% Barium Sulphate, 0.4% Bromocresol green and 2.5% Titanium Dioxide.

The sensing material may be applied to the selected length of the distal end by dipping the distal end in a solution of the sensing material. The duration of time for which the dipping should occur should be sufficient to cause the desired transformation, e.g. fluidization, of the distal end material but not so long so as to cause undesirable effects on the optical or chemical properties of the distal end material. For instance, prolonged exposure of certain polymers to certain solvent can cause brittleness, cracking and/or opacification and so the duration of exposure should be modified according to the material and solvent. Any undesirable reaction of the distal end material of the waveguide may be mitigated by minimizing the area of exposure of the distal end. For instance, the exposure may be constrained only to the tip of the waveguide. However, application to a greater length of the waveguide is desirable to increase the optical signal.

The distal end may preferably be dipped (e.g. vertically) into the sensing material and left submerged in the sensing material for a duration of between 0.5 and 1.5 seconds. The distal end is more preferably submerged in the sensing material for approximately 1.0 second.

Following dipping of the distal end, the distal end is preferably dried for between 1.5 and 2.5 seconds, at room temperature. The distal end is more preferably dried for approximately 2.0 seconds, at room temperature.

In an alternative embodiment, treating the distal end of the optical waveguide to mix the sensing material with the material of the optical waveguide comprises:

a. contacting the distal end of an optical fibre with a fluid coating composition, the fluid coating composition comprising the sensing material dispersed or dissolved in a solvent, wherein the solvent is capable of at least partially fluidising or swelling the distal end material of the optical fibre such that at least some mixing of the distal end material and sensing material occurs; and b. removing solvent from the fluid coating composition in contact with the distal end and solidifying the sensing distal end to provide an optical fibre having a sensing distal end comprising a distal end material and a sensing material mixed with the distal end material.

The duration of time for which the "contacting" should occur should be sufficient to cause the desired transformation, e.g. fluidization or swelling, of the distal end material but not so long so as to cause undesirable effects on the optical or chemical properties of the distal end material. For instance, prolonged exposure of certain polymers to certain solvent can cause brittleness, cracking and/or opacification and so the duration of exposure should be modified according to the material and solvent. Any undesirable reaction of the distal end material of the waveguide may be mitigated by minimizing the area of exposure of the distal end. For instance, the exposure may be constrained only to the tip of the waveguide. However, application to a greater length of the waveguide is desirable to increase the optical signal.

The skilled person will appreciate that "fluidizing" of the distal end material or forming a "fluid state" refers to wherein the solid distal end material becomes more fluid, which may be the result of partial dissolution, tackifying, gel formation, melting or the like. This therefore has the ability to allow for mixing of at least some of the sensing material and distal end material to provide a good bond. Swelling of the distal end material is also able to provide a similar result because this allows for the sensing material to become more readily intermingled within the distal end material, such as wherein polymer chains of the sensing material become intertwined with polymer chains of the distal end material.

In embodiments of the methods of manufacture above, the solvent may be any suitable solvent herein described, e.g. as described above. The solvent may suitably be an organic solvent. The organic solvent is suitably capable of at least partially fluidising or swelling the distal end material of the optical fibre. For instance, the solvent may comprise $C_{1-6}$ alcohols, $C_{1-6}$ ethers, halo-substituted $C_{1-6}$ hydrocarbons, or mixtures thereof. The solvent may be selected from one or more of chloroform, dichloromethane, hexafluoroisopropanol, THF, dioxane, ethanol and methanol, preferably wherein the solvent is DCM, chloroform, methanol or mixtures thereof, more preferably methanol.

The optical waveguide may be a waveguide according to any embodiment described above. The optical waveguide may comprise a single optical fibre operable as both an input and an output. Alternatively, the optical waveguide may comprise a plurality of optical fibres, wherein at least one optical fibre is operable as an input optical fibre and at least one optical fibre is operable as an output optical fibre. The optical waveguide may comprise a proximate end advantageously having an output connector operable to separate the optical waveguide into an input proximate waveguide end and an output proximate waveguide end and optically engage with a control unit, e.g. a control unit as hereinbefore described.

The method of manufacture may further comprise forming the device to have sufficient rigidity such that it is operable as a stiffener to facilitate insertion of the feeding tube into the human or animal body.

According to a further aspect of the present invention there is provided a method of manufacturing a control unit operable to activate a device according to any aspect or embodiment of the present invention described herein. The method typically comprises: providing an optical sensor (e.g. light detector) operable to detect the change in optical properties (e.g. change in hue, intensity, colour, etc.) at the distal end of the optical waveguide and provide an output capable of signaling a change in optical characteristics at the sensor to a user, and configuring the sensor at the proximal end of the waveguide to enable detection of a change in optical properties at the distal end. In embodiments, the method comprises providing a processor and an optical sensor (e.g. light detector), wherein the optical sensor is operable to detect the change in optical properties at the distal end of the optical waveguide, and the processor is operable to receive characteristics of the change in optical properties from the optical sensor; configuring the processor to: enable activation of the optical sensor to receive optical characteristics output from the device; determine an optical characteristic (e.g. RGB or hue, saturation, a lightness, etc.) of the received optical characteristics from the distal end; compare the determined optical characteristic relative to one or more predetermined characteristics; and indicate to a user upon detecting the one or more predetermined characteristics of the output signal to enable the user to determine whether or not the sensing distal end is positioned in the predetermined position of the human or animal body. In embodiments, the optical sensor is a light detector.

In an embodiment of the above method, the method comprises providing a processor, a light source, a light detector and a device connector; configuring the processor to: enable activation of the light source to cause illumination of the distal sensing end of the device; enable activation of the light detector to receive light output from the device; determine the colour of the received light; compare the determined colour relative to one or more predetermined colours; and indicating to a user upon detecting the one or more predetermined colours of the output light.

According to a yet further aspect of the present invention is provided a method for confirming the position of a placed feeding tube, comprising: disposing a feeding tube position confirmation device as described according to any aspect or embodiment described herein in a pre-positioned medical feeding tube; providing an optical sensor at a proximal end of the feeding tube position confirmation device, the optical sensor operable to detect a change in optical properties at the distal end of the optical waveguide, advancing the position of the distal end of the optical waveguide, monitoring an output from the optical sensor to detect a signal indicative of a change in optical properties of the sensing material at the distal end of the optical waveguide and determining whether the signal matches one or more predetermined characteristics indicative of a desired position of the sensing distal end.

In an embodiment, the method for confirming the position of a placed feeding tube comprises: providing a medical feeding tube position confirmation system as described according to any aspect or embodiment of the system of the invention herein, connecting the control unit to the feeding tube position confirmation device disposed in a pre-positioned medical feeding tube; activating the control unit to cause illumination of the sensing distal end of the position confirmation device; receiving an output light from the optical waveguide; processing one or more characteristics of the output light to determine whether it matches one or more predetermined characteristics indicative of the position of the sensing distal end; and indicating the position of the sensing distal end to a user.

Matching the one or more characteristics of the signal/output light to the predetermined characteristics may be indicative of the sensing distal end being disposed in an environment of pH 6 or less, e.g. pH 5.5 or less.

Alternatively, or additionally, matching the one or more characteristics of the signal/output light to the predetermined characteristics is indicative of the sensing distal end being disposed in an environment of pH 4 or less.

The sensing distal end is advantageously illuminated with a pulse of light (e.g. sent down the waveguide from an illumination source at the proximal end of the waveguide). The pulse of light is preferably in the range of 6 to 10 milliseconds in duration. The pulse of light is more preferably 8 milliseconds in duration.

The sensing distal end is advantageously illuminated with white light with a wavelength in the range of 405 nm to 685 nm.

Processing characteristics of the output light may comprise determining the intensity of the red, green and blue colours of the output light, i.e. the light output from the sensing distal end. For instance, if a colour change reaction takes place at the sensing distal end as a result of the waveguide being located as the desired location, the colour change reaction can be observed by way of a change in the optical characteristics of the light returning to the optical sensor at the proximal end of the waveguide.

Processing characteristics of the output light advantageously comprises determining values for the hue, saturation and lightness of the output light and comparing those values with predetermined values indicative of the distal sensing end being disposed in said predetermined position.

The processor advantageously confirms placement of the distal sensing end in the predetermined position upon determination that the hue is within a yellow colour parameter.

According to an further aspect of the present invention there is provided a feeding tube position confirmation device, operable to confirm the position of a predetermined portion of a medical feeding tube in a predetermined portion of a human or animal body, the position confirmation device comprising an optical waveguide dimensioned to be insertable into the lumen of said feeding tube, the optical waveguide having a sensing distal end comprising a sensing material operable to provide a change in optical properties at the distal end of the optical waveguide dependent on the environment to which the sensing distal end of the waveguide is exposed, wherein the sensing material comprises an optical indicator and a reflective material.

Typically, the sensing material is provided as a coating on the distal end of an optical fibre. The optical indicator may be any optical indicator as described herein, preferably a chemical indicator such as Bromocresol green.

The optical indicator may be mixed with a polymer (e.g. dispersed or dissolved within a polymer). The polymer may be any suitable polymer as described herein in respect of the sensing material polymer of any other aspect and embodiment. Preferably the polymer is a hydrophilic polyurethane, which may advantageously be a thermostable polyurethane.

In embodiments, the sensing material operable to provide a change in optical properties at the distal end of the optical waveguide is a sensing material operable to change to a predetermined colour relative to the chemical content of the environment to which it is exposed and thereby cause a change in the colour of light incident thereon dependent on the environment to which the sensing distal end of the waveguide is exposed, preferably wherein the sensing distal end of the optical waveguide comprises a chemical indicator, hydrophilic polyurethane and a reflective material.

For instance, in an embodiment there is provided a feeding tube position confirmation device, operable to confirm the position of a predetermined portion of a medical feeding tube in a predetermined portion of a human or animal body, the position confirmation device comprising an optical waveguide dimensioned to be insertable into the lumen of said feeding tube, the optical waveguide having a sensing distal end comprising a sensing material operable to change to a predetermined colour relative to the chemical content of the environment to which it is exposed and thereby cause a change in the colour of light incident thereon dependent on the environment to which the sensing distal end of the waveguide is exposed, preferably wherein the sensing distal end of the optical waveguide comprises a chemical indicator, hydrophilic polyurethane and a reflective material.

The chemical indicator may be any indicator hereinbefore described, and may optionally comprise at least one of: Thymol Blue, Methyl Red, Bromothymol Blue, Phenolphthalein, and Bromocresol.

The hydrophilic polyurethane is advantageously a thermostable polyurethane.

The reflective material may be any reflective material hereinbefore described, and may advantageously be Titanium Dioxide. The reflective material may be provided in the form of reflective particles. The particles may for instance have a maximum diameter of 100 μm or less, optionally 90 μm, 80 μm or less, 70 μm or less, 60 μm or less, 50 μm or less, 40 μm or less, 30 μm or less, 20 μm or less, or 10 μm or less. In embodiments, the mean particle diameter of the reflective particles is 50 μm or less, 40 μm or less, 30 μm or less, 20 μm or less, or 10 μm or less, e.g. 10 μm or less. In embodiments, the reflective material may be mixed with a polymer.

In embodiments wherein the sensing material comprises an optical indicator mixed with a polymer, the reflective material is preferably also mixed with a polymer, preferably the same polymer. For instance, the optical indicator and reflective material may be mixed or dispersed within the same polymer matrix.

The inventors have discovered that particularly advantageous effects can be obtained when a reflective material is provided with (preferably mixed with) an optical indicator in the sensing material according to this aspect and embodiments. In particular, the use of a reflective material mixed with the optical indicator at the sensing distal end of the waveguide improves the strength of the optical signal returning up the waveguide to be detected and is therefore eminently suitable for use with narrower diameter optical waveguides.

The sensing material may advantageously further comprise a brightening agent, such as any hereinbefore described, most preferably Barium Sulphate.

The sensing material may be as defined according to any of the aspects and embodiments of sensing material described herein above. The sensing material may advantageously contain 96% Hydrophilic Polyurethane polymer, 0.4% Barium Sulphate, 0.4% chemical indicator and 2.5% reflective material.

The chemical indicator and the reflective material may for instance be advantageously encapsulated within the matrix of a Hydrophilic Polyurethane polymer.

The feeding tube position confirmation device according to this aspect may be provided in the form of a kit or system as described above for other corresponding devices, and may likewise be the device used in the method of positioning a feeding tube position confirmation device as described herein.

The feeding tube position confirmation device according to this aspect and embodiments may be suitably manufactured by a method comprising: providing a length of optical waveguide having a proximal end and a distal end; providing a quantity of sensing material comprising an optical indicator (e.g. chemical indicator such as Bromocresol green) and reflective material (e.g. titanium dioxide) and treating the distal end of the optical waveguide to coat the distal end material of the optical waveguide with the sensing material. The sensing material used to the treat the optical fibre may for instance be in the form of a solution, gel, dispersion or suspension of the optical indicator, reflective material and a solvent, optionally further comprising a polymer. The solvent may suitably be any solvent described herein, and is preferably methanol.

In embodiments, the treating may cause the sensing material and distal end material to mix. For instance, the method of manufacture may be according to a method of manufacture as described above for other aspects and embodiments of the invention.

BRIEF DESCRIPTION OF THE DRAWINGS

The present invention will now be described with reference to the accompanying drawings, in which.

DETAILED DESCRIPTION

Figure 1:
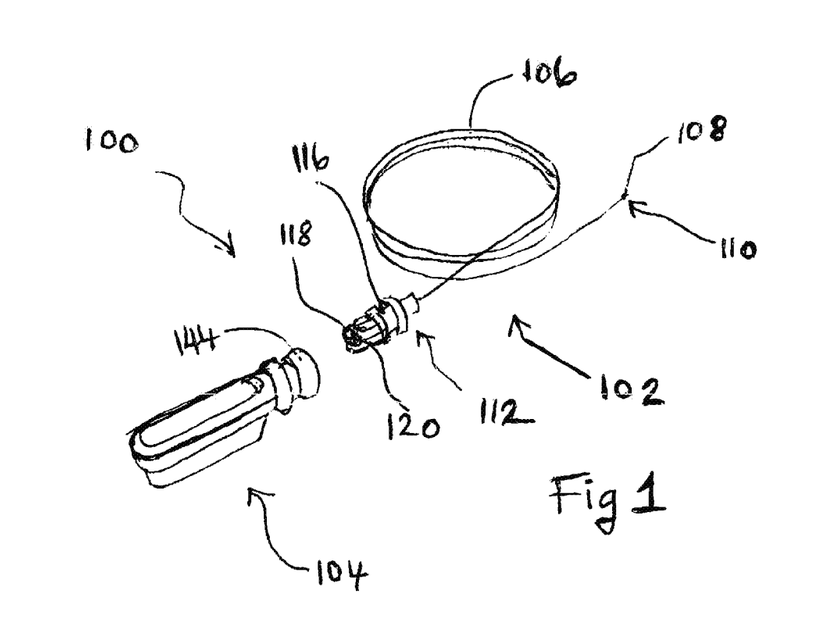
FIG. 1 is a drawing showing a feeding tube position confirmation system having a feeding tube position confirmation device and control unit, according to the present invention.
Figure 2:
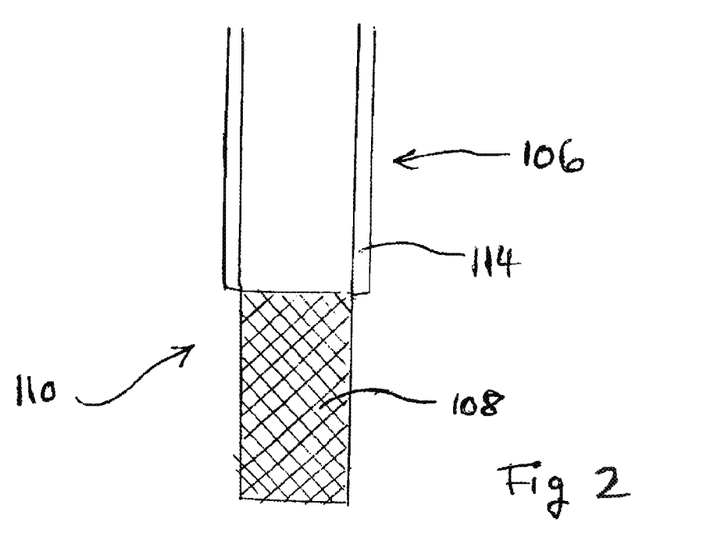
FIG. 2 is a drawing showing the distal sensing end of the feeding tube position confirmation device of FIG. 1.

Referring to FIGS. 1 and 2, a medical feeding tube position confirmation system 100 comprises a feeding tube position confirmation device 102 and a control unit 104.

The confirmation device 102 is a disposable single use device, comprising an optical waveguide 106 having a sensing distal end 108.

The optical waveguide 106 is a single plastic optical fibre which is of a length and diameter suitable for insertion into the lumen of a medical feeding tube (not shown), such as, for example, a nasal-gastric (NG) feeding tube.

Alternatively, the optical waveguide 106 may comprise a plurality of optical fibres, wherein at least one fibre is operable as an input optical waveguide and at least one fibre is operable as an output optical fibre. In an alternative embodiment the input and/or output waveguide may be a bundle of optical fibres. Also, as an alternative embodiment, the optical waveguide 106 may be formed from silica material.

The optical waveguide 106 has a distal end 110 and a proximate end 112.

The sensing distal end 108 is disposed on the distal end 110 of the optical waveguide 106 and comprises a sensing material bonded within the chemical structure of the optical waveguide 106, within, for example, the end 10 mm of the distal end 110, as can be seen in FIG. 2.

The sensing material comprises Thermo-stable Hydrophilic Polyurethane, Barium Sulphate, Bromocresol green and Titanium Dioxide and, more preferably, contains 96% Thermo-stable Polyurethane, 0.4% Barium Sulphate, 0.4% Bromocresol green and 2.5% Titanium Dioxide.

The Bromocresol green acts as a pH colour indicator and the Titanium Dioxide provides a reflective quality to the sensing material to facilitate reflection of the light being delivered along the optical waveguide 106. The Thermo-stable Polyurethane enables the sensing material to be workable and to facilitate bonding of the sensing material within chemical structure of the optical fibre material.

Although the sensing material has been described above using the chemical indictor, other chemical or biological indicators may be additionally or alternatively be used, such as for example Thymol Blue, Methyl Red, Bromothymol Blue, Phenolphthalein, Flourescein or Esther for example Triglycerides.

The chemical or biological indicator changes colour depending on the presence of specific predetermined markers such as, for example, pH level or Biological Markers such as Human Gastric Lipase, Pepsin, Intrinsic Factor, Mucin and Gastrin. The indicators are typically encapsulated within a crisscross matrix of polymer. Suitably, the polymer is porous and the compounds trapped within the matrix are too large to pass through the polymers pores. However, the pores are large enough to allow small molecules to pass through, absorbing into the polymer sensing matrix such as water and hydrochloric acid from the stomach.

The sensing distal end 108 is formed by stripping back approximately 10 mm of cladding 114 from the distal end of the optical waveguide 106, coating the stripped back distal end 110 with sensing material and leaving to dry before submerging the coated distal end 110 into a solvent such as, for example, a sodium hydroxide solution. The Sodium Hydroxide solution is advantageously a 0.01M Sodium Hydroxide solution.

The step of coating the stripped back distal end 110 with sensing material and leaving to dry may be undertaken by dipping the distal end 110 vertically into the sensing material, submerging the distal end 110 in the sensing material for between 0.5 and 1.5 seconds and more preferably approximately 1.0 second, removing and drying for between 1.5 second and 2.5 seconds, at room temperature, and more preferably approximately 2.0 seconds, at room temperature. The steps of applying the sensing material and drying can be repeated six times, for example, to ensure sufficient sensing material has been applied.

As an alternative, the sensing material can be applied to the distal end 110 using other methods, such as, for example, by spraying the sensing material.

When the sensing material has been applied to the distal end 110, the distal end may be submerged and soaked in sodium hydroxide solution, which acts to transform the BCG-coated distal end to a Blue colour thereby priming the material of the optical waveguide 106 to form a sensing distal end 108.

The coated distal end 110 is submerged in the sodium hydroxide solution from a duration of between 7 and 13 seconds and more preferably for approximately 10 seconds. Following removal of the distal end 110 from the sodium hydroxide, the sensing distal end 108 is dried for between 30 and 60 minutes, at room temperature, and more preferably approximately 45 minutes at room temperature.

Alternatively, the coated distal end 110 can be transformed into a more fluid state by heating it to a temperature in the range of between 175 to 250° C. and preferably to a temperature of approximately 232° C.

The proximate end of the optical waveguide 106 comprises a control unit connector 116. The control unit connector 116. The control unit connector 116 is operable to separate the optical waveguide into an input proximate waveguide end 118 and an output proximate waveguide end 120 which both and optically engage with the control unit 104.

The device 102 is formed with sufficient rigidity such that it is operable as a stiffener to facilitate insertion of the feeding tube into the human or animal body.

Figure 3:
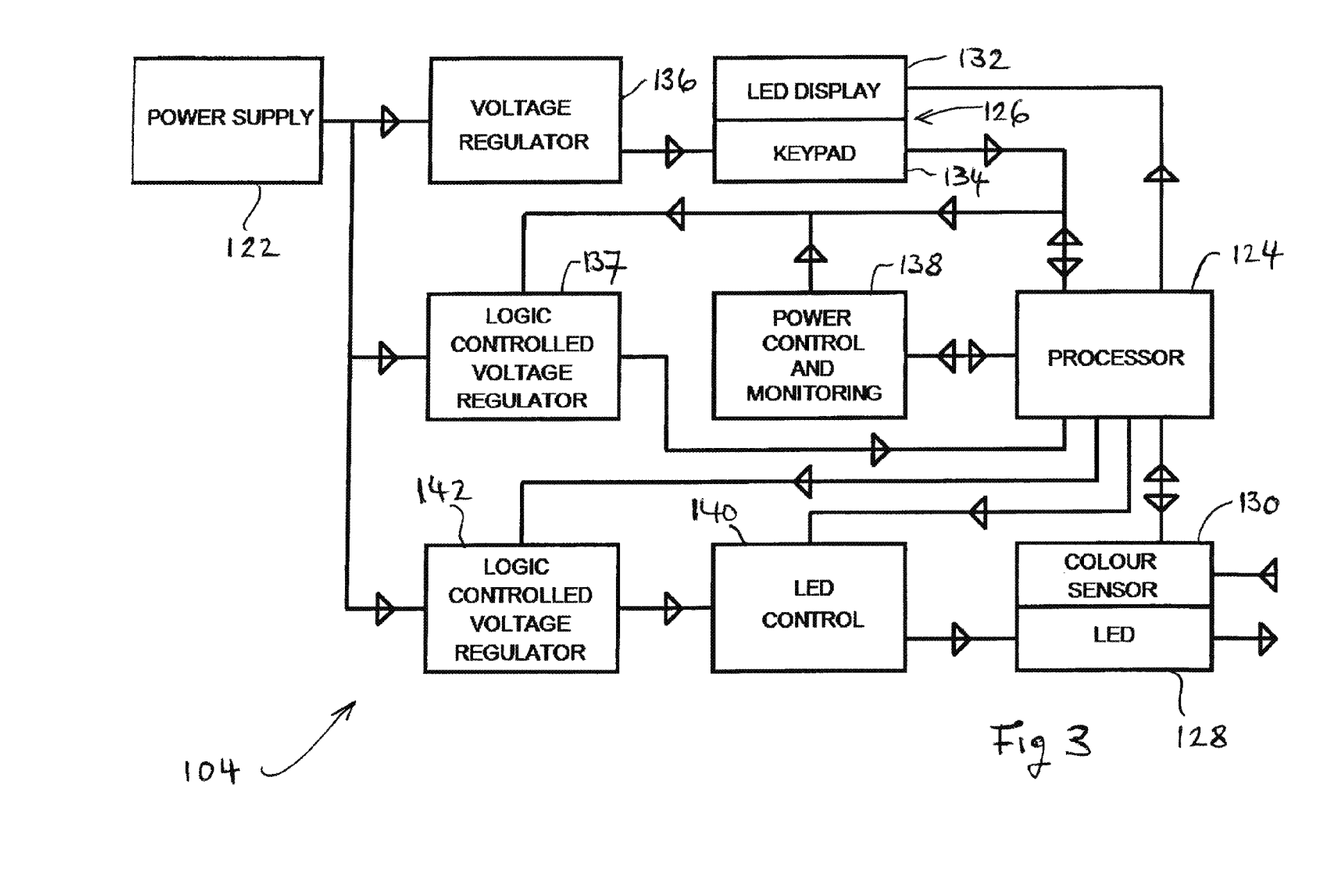
FIG. 3, is a schematic drawing of the general components of the control unit of FIG. 1.

Referring to FIG. 3, in general, the control unit 104 comprises a power supply 122, a processor 124, a user interface 126, a light source 128 and a light detector 130.

The user interface 126 comprises a user output interface 132, such as an LED display indicator, and a user input interface 134, such as a dedicated keypad. A voltage regulator 136 regulates the voltage applied to the user interface 126. The user output interface 132 and the user input interface 134 are connected to the processor 124 to receive signals from the processor and to activate the control unit, respectively.

A first logic controlled voltage regulator 137 is operable to regulate the voltage for the processor 124. A power controller and monitor 138 controls and monitors the power and taps into the processor 124 and logic controlled voltage regulator 136 loop.

The light source 128 is suitably a light emitting diode (LED) light source, operable to deliver white light with a wavelength in the range of 405 nm to 685 nm. The light source 128 is controlled by an LED controller 140. The LED controller is connected to receive signals from the processor 124. The LED controller is regulated by a second logic controlled voltage regulator 142, which is powered by the power supply 122 and connected to receive signals from the processor 124.

The light detector 130 is connected to pass signals to and from the processor 124. The light detector is a RGB colour sensor.

Referring also to FIG. 1, the control unit 104 further comprises a device connector 144, which houses the light source 128 and the light detector 130. The device connector 144 is formed to provide a mechanical detachable attachment with the control unit connector 116, of the device 102, such that the light source 128, of the control unit 104, optically aligns with the input proximate waveguide end 118 and the light detector 130, of the control unit 104, optically aligns with the output proximate waveguide end 120.

Figure 4:
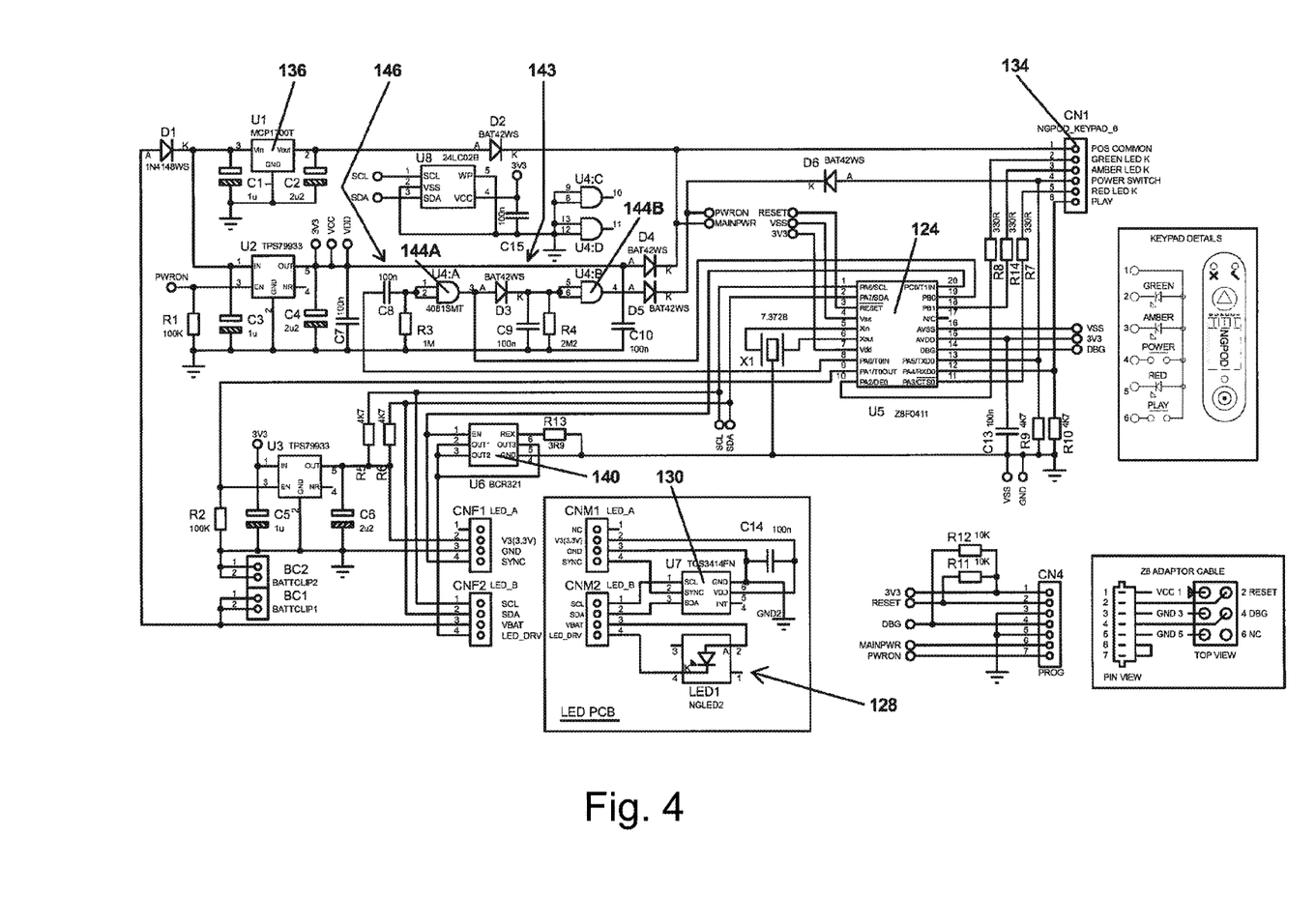
FIG. 4 is a circuit diagram of the control unit of FIG. 3.

Referring also to FIG. 4, the circuitry and operation of the control unit will now be described in more detail.

Voltage is supplied from a 6 volt battery through a reverse polarity diode D1. Capacitors, C1-C6, provide supply decoupling and contribute to the suppression of noise generated by the regulators, (136, 137, 142). In FIG. 4, the voltage regulator 136 is a 1.8 v voltage regulator U1, and the first and second logic controlled voltage regulators, 137 and 142, are 3.3 v logic controlled voltage regulators U2 and U3, respectively. The output of voltage regulator 136 is fed to the user input interface 134 and user output interface 136 through a diode D2.

Upon a user activating the control unit through the user input interface 134, voltage from the voltage regulator 136 is fed to enable pin regulator 137. Resistor R1 pulls the enable pin low and ensures voltage regulator 137 is disabled when the enable signal is removed. Voltage regulator 137 supplies power to the processor 124 and a watchdog circuit, WD, built around a CMOS AND Gate 144. A pulse train is generated from pin 8 of the processor 124, which feeds the watchdog circuit, WD, input. The output of the watchdog circuit, WD, remains high for the duration that the pulse train is present.

The pulses are fed to a differentiator circuit 146 formed by capacitor C8 and resistor R3. Capacitor C8 blocks DC to the input of the CMOS AND Gate 144, but allows the pulses to pass. CMOS AND Gate 144A buffers the pulses and charges capacitor C9 via diode D3. Resistor R4 gradually discharges capacitor C9 in between the charging pulses. The pulse period of the processor 124 and the time constant of capacitor C9 and resistor R4 is such that the voltage on capacitor C9 is maintained above the threshold voltage of CMOS AND Gate 144B. The output of CMOS AND Gate 144B therefore remains high.

The output of CMOS AND Gate 144A also feeds pin 18 of the processor 124 so that the pulses can be monitored. If the pulses stop due to CMOS AND Gate 144 or processor 124 failure, an error is generated and the control unit shuts down.

The watchdog circuit, WD, output feeds the first logic controlled voltage regulator 137 enable pin via diode D5 and thereby keeps the first logic controlled voltage regulator 137 active. This output also feeds the user interface 132 via diode D4 taking over from the voltage regulator 136, diode D2 blocking the voltage from feeding into the voltage regulator 136 output.

If the processor 124 fails and the pulse train ceases, the static voltage level could be either high or low. However, due to the DC blocking action of capacitor C8, the input to the CMOS AND Gate 144A will always be 0 v. The voltage across capacitor C9 will discharge via resistor R4 and will drop below the threshold voltage of the CMOS AND Gate 144B. The output of the CMOS AND Gate 144B will go low, removing the enable signal from the first logic controlled voltage regulators 137, prevent power being delivered to CMOS AND Gate 144 and processor 124.

The user input interface 134 is read by input pin 12 of the processor 124. Resistor R10 pulls the pin low when the user interface 134 is not activated. When the user input interface 134 is activated, pin 9 of the processor 124 enables the second logic controlled voltage regulator 142 to supply power to the light detector 130. Pin 20 of the processor enables the LED controller 140 to drive the LED light source 128. The current is set by resistor R13.

The light detector communicates with the processor using I2C protocol. Resistors R5 and R6 provide termination for the SCL and SDA signals.

The unused input pins of the CMOS AND Gate 144 are tied to 0 v for integrated circuit stability.

Resistors R7 and R8 limit current to the red and green LEDs from the processor 124 pins 10 and 11.

BC1 and CN1-CN6 are connectors for electrically connecting the different circuit boards to each other.

A medical feeding tube position confirmation kit comprises a medical feeding tube and at least one feeding tube position confirmation device 102. The kit may also include a control unit 104

A medical feeding tube position confirmation system comprises at least one feeding tube position confirmation device 102 and a control unit 104

Referring to FIGS. 1 to 4, in use, the feeding tube position confirmation system 100 is used to confirm the position of a pre-inserted feeding tube. In such a procedure, the device 102 can be pre-inserted in the feeding tube or it can be inserted after insertion of the feeding tube into the patient has been undertaken Either way, the user connects the control unit connector 116 and the device connector 144 such as to cause the light source 128, of the control unit 104, to optically align with the input proximate waveguide end 118 and the light detector 130, of the control unit 104, to optically align with the output proximate waveguide end 120.

With the device 102 inserted in the feeding tube the distal sensing end 108 is positioned at the distal end of the feeding tube, adjacent the feeding tube feeding apertures The user then activates the input interface 134 causing the control unit 104 to operate, as described above with reference to FIGS. 3 and 4, to provide a white pulsed light to be launched from the light source 128, along the optical waveguide 106 to illuminate the distal sensing end 108

Where an NG feeding tube is being inserted, the distal end of the feeding tube should be correctly positioned in the stomach. As is known, the stomach is significantly more acidic than the upper digestive tract.

Upon entering an environment, such as the stomach, in which the pH is acidic, for example, 6 or less, the sensing material changes colour to a predetermined colour indicative of the distal sensing end and therefore the distal end of the feeding tube, being positioned in the stomach. In such as case, the pulses of white light, incident on the distal sensing end 108, is reflected back along the optical waveguide 106 as the predetermined colour. The reflected light is detected by the light detector and the characteristics of the coloured reflected light are determined. The characteristics may include one or more of hue, saturation and/or lightness (i.e. "HSL" values). The HSL values can be derived from the RGB values based on well-known calculations, such as those described in (Hanbury, A. (2008), Constructing Cylindrical Coordinate colour spaces. Pattern Recognition Letters, 494-500, which calculations are incorporated herein by reference). Where the sensing material comprises Bromocresol green, and the hue is determined as falling within a yellow colour parameter then the distal sensing end 108 can be considered to be placed in an acidic environment indicative that the feeding tube is correctly placed in the stomach of the patient. Upon the processor 124 determining that the hue of the reflected light falls within a yellow colour parameter it activates the user output interface 132 to signal to a user that the feeding tube is correctly positioned in the stomach and the user can commence with feeding the patient.

According to the present invention, as described herein, different pH values or chemical or biological characteristics can be used to confirm the position of a tube as a different colour hue of the reflected light can be determined which would be indicative of a different pH, for example, pH 5.5 or 4, or a different chemical or biological characteristic.

Experimental Methods

Preparation of Polyurethane-Coated Optical Fibres

Hydrophilic polyurethane pellets were mixed with a solvent to provide a concentration equivalent to 1 g of polyurethane per 20 mL solvent as a solution/suspension. This was performed in chloroform (at room temp), dichloromethane ("DCM") (room temp), hexafluoroisopropanol (room temp), ethanol (at 92° C.) and methanol (at 81° C.). Solvents were acquired from Sigma Aldrich and were typically ACS grade.

The exposed tips of polymethylmethacrylate optical fibres were incubated in 2 mL solvent for 5 min before dipping the fibres in the suspension/solution of polyurethane in solvent. The coated fibres were dried overnight at room temperature after being removed from the suspension/solution.

All the above solvents formed a cloudy suspension of polyurethane and provided a coated optical fibre. However, chloroform and DCM provided some undesirable whitening of the PMMA fibres corresponding to some brittling and opacification. Exposure of the fibres to these solvents should therefore be minimized in duration and area if these solvents are used. None of the alcohols tested displayed this whitening. However, some surface imperfections were observed on the coated fibres formed using hexafluoroisopropanol and ethanol (e.g. inhomogeneities of colour and texture). Methanol is thus a preferred solvent. The methanol solution appears to be less 'sticky' than its DCM counterpart, meaning at more concentrated solutions after being dipped there is no 'tailing' effect as can be seen with DCM solutions of a similar concentration. This effect is expected to allow for increased numbers of fibres to be dipped closer together simultaneously as they as they will be less prone to sticking together than with other solvents, e.g. DCM. Methanol not only therefore provides improved results in coating the PMMA fibres, but is cheaper than DCM, less environmentally toxic, has a slower evaporation rate and easier to handle from a manufacturing perspective.

Preparation of Bromocresol Green (BCG) Coated Optical Fibres

A similar method as above was used to coat PMMA fibres with BCG. BCG sol-gel pellets were obtained from IPC, Ireland. Methanol was obtained from Sigma Aldrich, UK). 1 g BCG sol-gel pellets were added to 10 mL, 15 mL, 20 mL, 25 mL or 30 mL methanol and stirred at 81° C. until pellets dissolved (approx. 10-30 min)). PMMA fibres were prepared by cutting and polishing 1 m length of bare PMMA fibre. One end of each fibre (i.e. the distal end) was then dipped (vertically) for 1 s into the respective BCG sol solution and removed to leave a coating of BCG solution on the distal end of the fibre. Fibres may be dipped multiple times to increase the coating amount. In such examples, the fibre was removed 1 s after dipping for a duration of 1 s before dipping again for 1 s. The process may be repeated as desired before leaving the fibres to dry at room temperature.

Testing of Coated Fibres

Coated fibres were tested by connecting the fibre to a control unit as described herein. A light source is activated to send light from the proximal end of the fibre down the waveguide fibre to the BCG-coated distal end. The output signal returning to the light detector from the distal end was monitored. The tip of the BCG-coated fibre was then immersed in a solution of pH 3. The output signal was then monitored for changes in hue over time. A solution of pH 3 causes a change in colour of BCG at the distal end from blue to yellow resulting in a detectable change in hue.

Method for Testing Compatibility of the Distal End Material of the Optical Fibre with the Solvent Optical fibres were cut to lengths of ~5 cm and a 1 cm length of the outer sheath removed from the tip to expose the inner PMMA fibre. The exposed PMMA fibre tip was immersed in ~1 mL of solvent and left for 1 hour at room temperature. Chloroform and dichloromethane caused whitening of the PMMA associated with increased brittleness and opacification. No whitening was observed with hexafluoroisopropanol, ethanol or methanol.

The invention claimed is:

1. A feeding tube position confirmation device, operable to confirm the position of a predetermined portion of a medical feeding tube in a predetermined portion of a human or animal body, the position confirmation device comprising an optical waveguide dimensioned to be insertable into the lumen of said feeding tube, the optical waveguide having a sensing distal end comprising a sensing material operable to provide a change in optical properties at the distal end of the optical waveguide dependent on the environment to which the sensing distal end of the waveguide is exposed, wherein the sensing material comprises an optical indicator and a reflective material, wherein the optical indicator and the reflective material are mixed with a hydrophilic polyurethane.

2. A device according to claim 1, wherein the sensing material is operable to change to a predetermined colour color dependent on the environment to which the sensing distal end of the waveguide is exposed.

3. A device according to claim 1, wherein the sensing material comprises a chemical or biological indicator and the chemical or biological indicator comprises at least one of: Thymol Blue, Methyl Red, Bromothymol Blue, Phenolphthalein, Bromocresol green, Fluorescein, Ether, and Universal Indicator.

4. A device according to claim 1, wherein the reflective material is titanium dioxide.

5. A device according to claim 1, wherein the sensing distal end of the optical waveguide is formed by coating the distal end of an optical waveguide with the sensing material, transforming the coated distal end into a fluid state such that the sensing material and distal end material are mixed with each other and then transforming the material into a solid state to form the sensing distal end.

6. A device according to claim 1, wherein the optical waveguide comprises an optical sensor at the proximal end of the optical waveguide operable to detect the change in optical properties at the distal end of the optical waveguide.

7. A medical feeding tube position confirmation kit comprising a medical feeding tube and at least one feeding tube position confirmation device as claimed in claim 1.

8. A medical feeding tube position confirmation system comprising a device as claimed in claim 1 and a control unit operable to control the device.

9. A method for confirming the position of a placed feeding tube, comprising: disposing a feeding tube position confirmation device according to claim 1 in a pre-positioned medical feeding tube; providing an optical sensor at a proximal end of the feeding tube position confirmation device, the optical sensor operable to detect a change in optical properties at the distal end of the optical waveguide, advancing the position of the distal end of the optical waveguide, monitoring an output from the optical sensor to detect a signal indicative of a change in optical properties of the sensing material at the distal end of the optical waveguide and determining whether the signal matches one or more predetermined characteristics indicative of a desired position of the sensing distal end.

* * * * *